(12) United States Patent
Blain et al.

(10) Patent No.: US 8,864,767 B2
(45) Date of Patent: Oct. 21, 2014

(54) ROD REDUCER INSTRUMENT FOR SPINAL SURGERY

(75) Inventors: Jason Blain, Encinitas, CA (US); Eric Kovach, Carlsbad, CA (US); Matt Lake, Carlsbad, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 1095 days.

(21) Appl. No.: 12/268,312

(22) Filed: Nov. 10, 2008

(65) Prior Publication Data

US 2010/0121385 A1 May 13, 2010

(51) Int. Cl.
*A61B 17/70* (2006.01)

(52) U.S. Cl.
CPC ................................ *A61B 17/7086* (2013.01)
USPC ........................................................ 606/86 A

(58) Field of Classification Search
USPC ........................................ 606/86 A, 246–279
See application file for complete search history.

(56) References Cited

U.S. PATENT DOCUMENTS

| | | |
|---|---|---|
| 3,604,487 A | 9/1971 | Gilbert |
| 4,411,259 A | 10/1983 | Drummond |
| 5,020,519 A | 6/1991 | Hayes et al. |
| 5,364,397 A | 11/1994 | Hayes et al. |
| 5,449,361 A | 9/1995 | Preissman |
| 5,720,751 A | 2/1998 | Jackson |
| 5,782,830 A | 7/1998 | Farris |
| 5,810,878 A | 9/1998 | Burel et al. |
| 5,910,141 A | 6/1999 | Morrison et al. |
| 6,440,133 B1 | 8/2002 | Beale et al. |
| 6,660,006 B2 | 12/2003 | Markworth et al. |
| 6,790,209 B2 | 9/2004 | Beale et al. |
| 2003/0009168 A1* | 1/2003 | Beale et al. ............... 606/61 |
| 2003/0225408 A1* | 12/2003 | Nichols et al. ............ 606/61 |
| 2006/0079909 A1* | 4/2006 | Runco et al. ............... 606/99 |
| 2007/0270867 A1* | 11/2007 | Miller et al. .............. 606/86 |
| 2007/0270869 A1* | 11/2007 | Young et al. .............. 606/86 |

FOREIGN PATENT DOCUMENTS

DE 4238339 5/1994

\* cited by examiner

*Primary Examiner* — Jerry Cumberledge
*Assistant Examiner* — Nicholas Plionis
(74) *Attorney, Agent, or Firm* — Knobbe, Martens, Olson & Bear, LLP

(57) ABSTRACT

A rod reducer instrument is configured to be secured to a fixation element and to force a rod into engagement with the fixation element. The rod reducer instrument can have a pliers to secure the rod reducer to the fixation element and a threaded shaft with a handle and a pusher member. The pliers can form a threaded channel that engages the threaded shaft and directs a movement of the shaft. The threaded shaft can translate a rotational movement at the handle into a linear movement at the pusher member and in this way force a rod into engagement with a fixation element.

20 Claims, 10 Drawing Sheets

ROD REDUCER INSTRUMENT FOR SPINAL SURGERY

CROSS-REFERENCE TO RELATED APPLICATIONS

N/A

BACKGROUND OF THE INVENTION

1. Field of the Invention

The present invention concerns surgical instruments for moving one part of a surgical implant into adjacent position or contact with another. In particular, the invention contemplates rod reducer instruments for use in placing or moving an orthopedic rod toward a bone fixation element.

2. Description of the Related Art

In orthopedic surgery, and particularly in spinal surgery, it is well known to correct an injury, malformation, or other defect using an implanted rod affixed to a body part to be corrected. For example, rod systems have been developed for correcting the positioning of and stabilizing of the spine, and for facilitating fusion at various levels of the spine. In one such system, the rod or elongated implant can be disposed longitudinally along a length of the spine. The rod can be bent, either prior to or during surgery, to correspond to the normal curvature of the spine in the particular region being instrumented, or to such other curvature as the surgeon may deem appropriate to correct the defect. For example, the rod can be bent to form a normal kyphotic curvature for the thoracic region of the spine, or to form a normal lordotic curvature for the lumbar region. The rod can then be attached or engaged to a number of fixation elements which have been inserted or implanted into the vertebrae along the segment of the spinal column.

Fixation elements are well know in the art and can include all types of bone screws, hooks, bolts, etc. configured to engage the vertebrae. For instance, one such fixation element is a laminar hook, configured to engage a lamina of the vertebra. Another prevalent fixation element is a spinal screw which can be threaded into a pedicle or other portion of vertebral bone. An alternative type of fixation element is a multi-axial bone screw.

In one typical spinal procedure, a rod is coupled to two or more bone screws that are fixed to opposite sides of the spine or spinous processes. The bone screws are first threaded into a portion of several vertebral bodies, such as the pedicles of these vertebrae. The rod is coupled to the bone screws to provide corrective and stabilizing forces to the spine. Affixing a rod to a bone screw generally requires the rod to be in close adjacent position or in contact with the screw. This may require that the rod and implanted bone screw be moved with respect to each other so that the rod occupies space within a channel or other opening in the screw. The rod can then be coupled to the implanted bone screw using a set screw, plug or other appropriate fastener. The process of placing a rod within or adjacent to an implanted fixation element so that they can be coupled together is termed "reducing" the rod.

Rod reduction is commonly performed by a surgeon using his or her hands and/or rigid tools such as pliers, levers or other instruments able to create the necessary pushing and/or pulling forces on the implanted fixation element and rod. Such procedures generally require the surgeon to place the rod directly over the implanted fixation element, intersecting a longitudinal axis of the fixation element. Consequently, access to the rod and the implanted fixation element along that axis, i.e. directly above the opening in the fixation element into which the rod is to be placed, can be necessary or at least highly desirable. However, such access can be difficult depending on such factors as the malformation to be corrected and the overall physiology of the patient. Additionally, as surgical procedures are generally encouraged to be minimally invasive, access can be very difficult as a result of the small ports or incisions of such procedures. Additionally, with use of mono-axial screws, the physiology of the patient can require that the screw be placed at an angle such that the surgeon would have difficulty accessing and exerting force in the necessary orientation on the rod and/or fixation element. With multi-axial fixation devices, the orientation of an unsecured rod-receiving part of the fixation element can be even more varied with respect to the rod and/or the surgeon. Consequently, the surgeon is still frequently faced with the task of reducing a rod from an awkward angle.

Various attempts in the prior art have been made in providing rod reducing instruments, for example, the rod reducer instrument disclosed in U.S. Pat. No. 6,790,209 to Beale. The rod reducer of Beale utilizes a pliers arrangement to reduce a rod. Rod reducing pliers of this type can be difficult to use as the amount of pressure required to reduce the rod may depend on the particular fixation element and rod and may be difficult for particular users without great hand strength. Therefore there exists a need for a more efficient and easier to use rod reducing instrument that can be used efficiently, safely and securely in rod reduction procedures and for rod reduction instruments that can be used in both minimally invasive and open surgical approaches to the site of rod attachment.

SUMMARY OF THE INVENTION

A rod reducer instrument for use in orthopedic surgery according to some embodiments can comprise a pliers, a pushing member, a threaded shaft and a shaft handle. The pliers can be configured for gripping an orthopedic screw and comprise a pair of grips, a pivot and a head having gripping jaws. The grips can be configured for opening and closing the pliers and configured to combine to form a threaded channel. The pushing member can be configured to force a rod into engagement with the orthopedic screw. The threaded channel can be configured to engage the threaded shaft when the pliers are closed. The shaft handle can be configured to rotate the threaded shaft and thereby cause the pushing member to experience linear motion to force the rod into engagement with the orthopedic screw. One side of the pair of grips can form part of the threaded channel and one side of the other of the pair of grips can form the other part of the threaded channel.

Certain embodiments of a rod reducer instrument can further comprise a rotational joint connecting the pushing member and the threaded shaft. The pushing member can be between the gripping jaws. The pushing member can be configured to only engage a top of the rod. In some embodiments the pushing member can comprise an orifice configured to engage with a fixed pin and guide the linear movement of the pushing member. According to some embodiments the pivot can also function as the fixed pin.

In some embodiments, a rod reducer instrument for use in orthopedic surgery can comprise a pliers, a pushing member and a handle. The pliers can comprise first and second elongated members, a pair of grips for opening and closing the pliers, a pivot and a head having gripping jaws. The pushing member can be between the gripping jaws, configured to force a rod into engagement with an orthopedic screw and being slidable on the pivot of the pliers. The handle can be configured to turn in a circular rotation. The rod reducer can further be configured to convert the circular rotations of the handle into a linear motion experienced by the pushing member and to thereby force the rod into engagement with the orthopedic screw.

Some embodiments can further comprise a threaded shaft wherein the first and second elongated members can be configured to form a threaded channel to engage the threaded shaft when the grips are closed. The pivot of the rod reducer can have a stepped outer perimeter with a first step outer perimeter having a circular diameter so that the first elongated member can rotate about the pivot, a second step outer perimeter configured to substantially conform within an orifice in the second elongated member, the second elongated member not rotating about the pivot and a third step outer perimeter configured to engage the pushing member, the pushing member being slidable upon the pivot.

Certain embodiment can comprise a method of reducing a rod in orthopedic surgery. The method can comprise the steps of engaging a rod with a pushing member of a rod reducer instrument, the rod reducer further comprising a pliers and a handle, closing the pliers to grip an orthopedic screw and to form a threaded channel with the pliers, rotating the handle in a continuous circular rotation to cause a downward linear movement of the pushing member through the threaded channel and forcing the rod into engagement with the screw. The method can further comprise locking the pliers in gripping engagement with the orthopedic screw.

According to some embodiments, the method can further comprise unlocking the pliers from gripping engagement with the orthopedic screw and thereby releasing engagement with the rod. In certain embodiments, the method further comprises adjusting a relationship between the pushing member and the pliers. The step of rotating the handle can further comprise causing a downward linear movement of the pushing member through the threaded channel and between jaws of the pliers.

DETAILED DESCRIPTION OF THE PREFERRED EMBODIMENT

Figure 1:
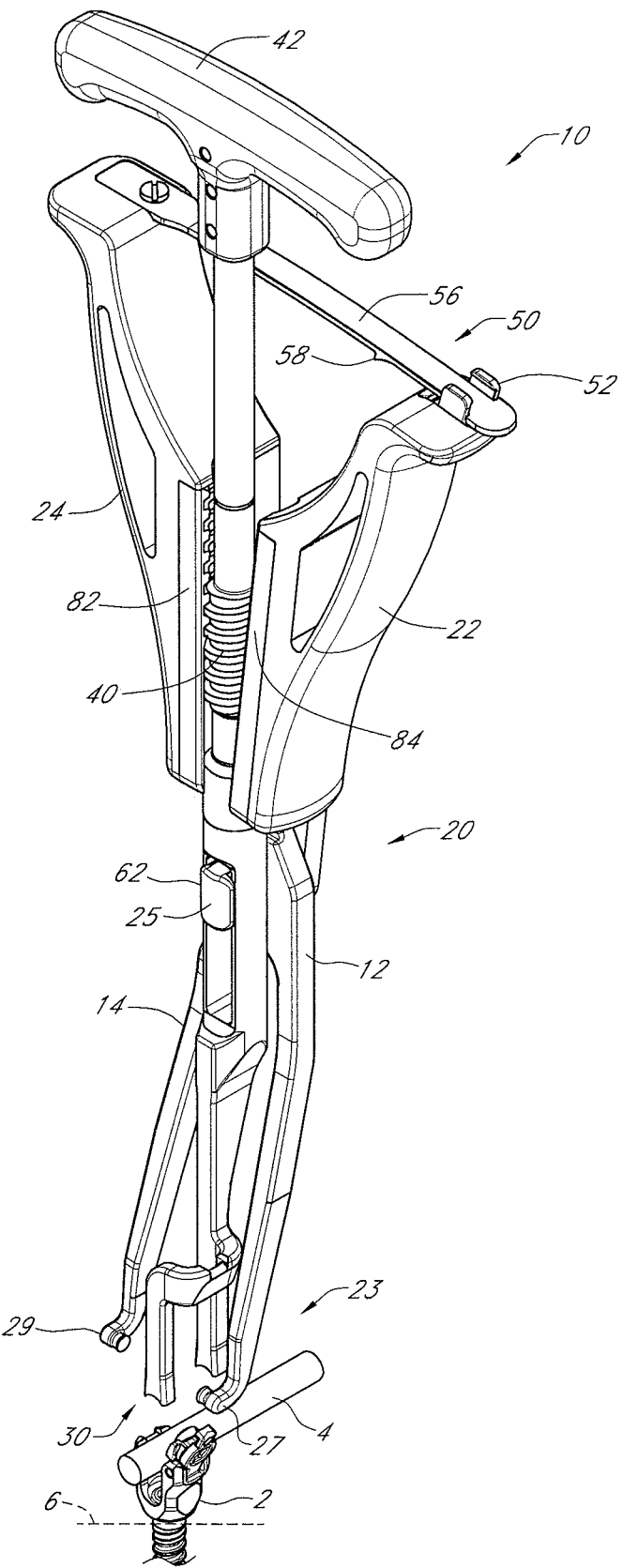
FIG. 1 illustrates a perspective view of a rod reducer instrument according to one embodiment.

A rod reducer instrument 10 according to one embodiment is illustrated in FIG. 1. The rod reducer instrument or rod reducer 10 can be used to engage a fixation element 2 and a rod 4 to reduce the rod 4, or force the rod 4 into engagement with the fixation element 2.

Figure 2:
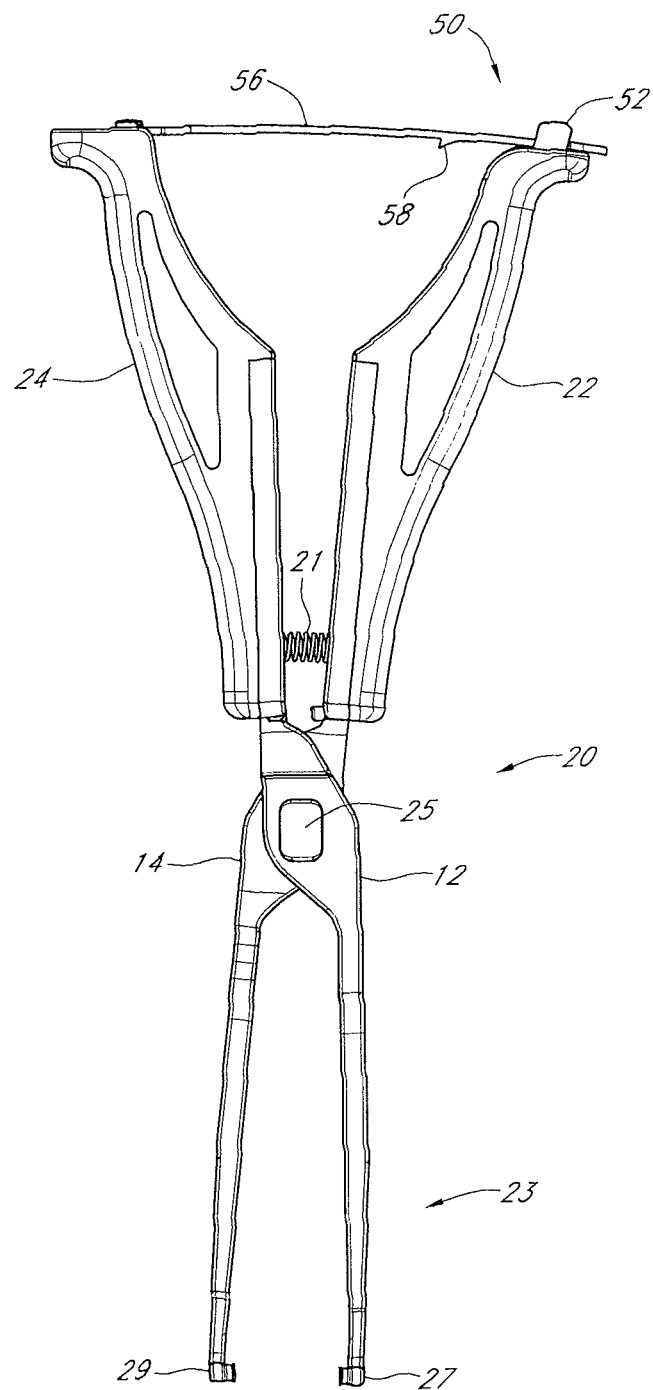
FIG. 2 is a front view of a rod reducer instrument showing the pliers, with a shaft and handle removed.

A simple overview of how a rod reducer instrument 10 according to one embodiment can be used will now be explained with reference to FIGS. 2-3. FIG. 2 shows a partially disassembled rod reducer 10 with a pliers 20 and some other features remaining. The pliers 20 can be used to engage and secure the rod reducer 10 to a fixation element 2, such as a bone screw. A pliers locking device 50 is also shown. The pliers locking device 50 can lock the pliers 20 in a closed position so that it is unnecessary for a user to continue to apply force to the pliers 20 to maintain the pliers 20 in the closed position. It is envisioned that a user may want to lock the pliers 20 in the closed position once the pliers 20 have been engaged with and secured to a fixation element 2.

Figure 3:
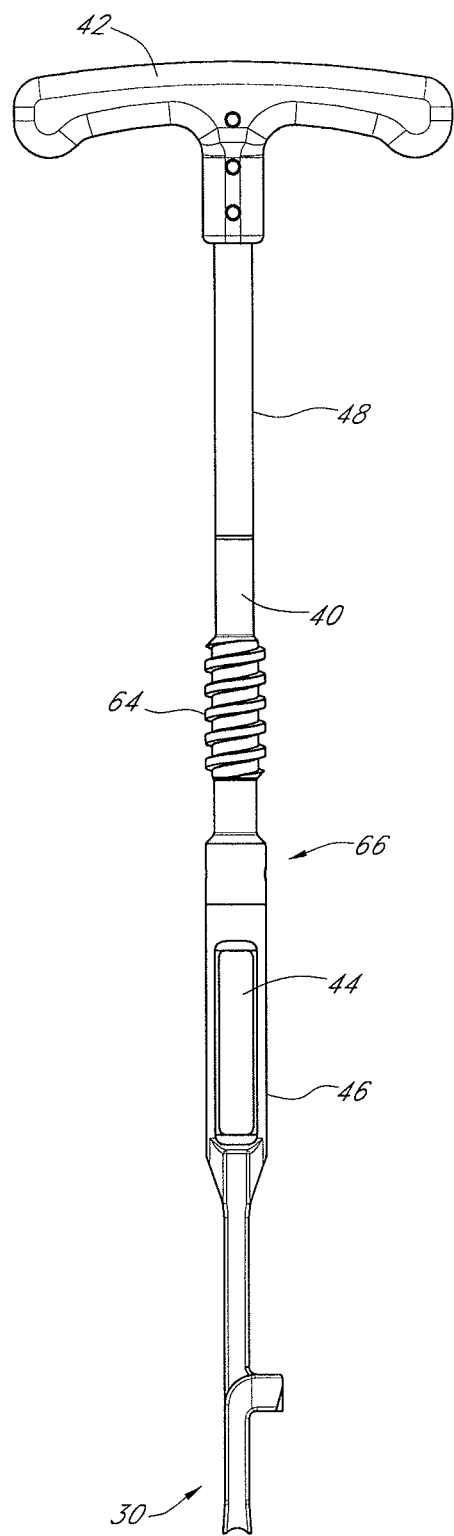
FIG. 3 is a shaft and handle from a rod reducer instrument.

Now turning to FIG. 3, a shaft 40 and a handle 42 from a rod reducer instrument 10 is shown. At one end of the shaft 40 is a pushing member 30. The pushing member 30 can be used to engage a rod 4. The pushing member 30 can further be used to force the rod 4 into engagement with a fixation element 2 as described above with regard to the pliers 20. FIG. 3 also shows a handle 42 at the opposite end of the shaft 40 from the pushing member 30. The handle 42 can be rotated to cause the shaft 40 to move in a downward direction and to cause the pushing member 30 to exert a downward force on the rod 4 or any other device engaged by the pushing member 30.

Now that a general and simplified overview has been given of the rod reducer instrument 10, the instrument, its parts and the interaction of its parts will be described in more detail. Returning to FIG. 1 and also referencing FIGS. 4-6, an embodiment of a rod reducer instrument 10 will be described. A rod reducer 10 can comprise a pliers 20, a pushing member 30 and a shaft 40.

The pliers 20 can be configured to engage a fixation element 2. The pliers 20 can be configured to secure the rod reducer instrument 10 to a fixation element 2. The pliers 20 can comprise grips 22, 24, a pivot 25 and a head 23. The pliers 20 can further comprise a spring 21.

The grips 22, 24 can be configured to open and close the pliers 20. The grips 22, 24 can be made out of various materials including metal or plastic. The grips 22, 24 as well as other parts of the rod reducer instrument are preferably made from materials suited for a surgical environment. The grips 22, 24 can be contoured to fit a user's hand and to better transfer a closing force at the grips 22, 24 to the head 23. Other embodiments can comprise other styles of pliers 30 or other mechanisms to secure the rod reducer to a fixation element 2.

The head 23 can comprise jaws 27, 29. The jaws 27, 29 can be configured to grip a fixation element 2. The jaws 27, 29 can be configured to grip a particular type of fixation element or can be configured to grip different types of fixation elements. As shown, the jaws 27, 29 have circular protrusions projecting towards a gripping area. Protrusions on the jaws 27, 29 can allow the jaws 27, 29 to attach to the sides of a fixation element 2 and can be ideally suited for fixation elements 2 with recesses on their sides. If the fixation element 2 has a recess on the side, the protrusion can take advantage of the recess by protruding into the recess and still engage with the fixation element 2. Additionally, the rod reducer 10 can take further advantage of this feature by leveraging the interaction of the top of the protrusions and the top of the recesses to help ensure that the rod reducer 10 remains secure as a downward force is exerted on a rod 4 to reduce the rod 4. In other embodiments, the fixation element 2 can have a top lip such that the top of the protrusions on the jaws 27, 29 can engage with the top lip. The jaws 27, 29 can have flat surfaces, ridges or treads on the surface to create greater friction or traction between the jaws 27, 29 and the fixation element 2. In other embodiments, the jaws 27, 29 can engage a fixation element 2 at a recess and/or outside of a recess. In some embodiments, independent of whether the fixation element 2 has a recess or not, the jaws 27, 29 can engage the fixation element 2 on the sides of the fixation element 2.

Figure 4:
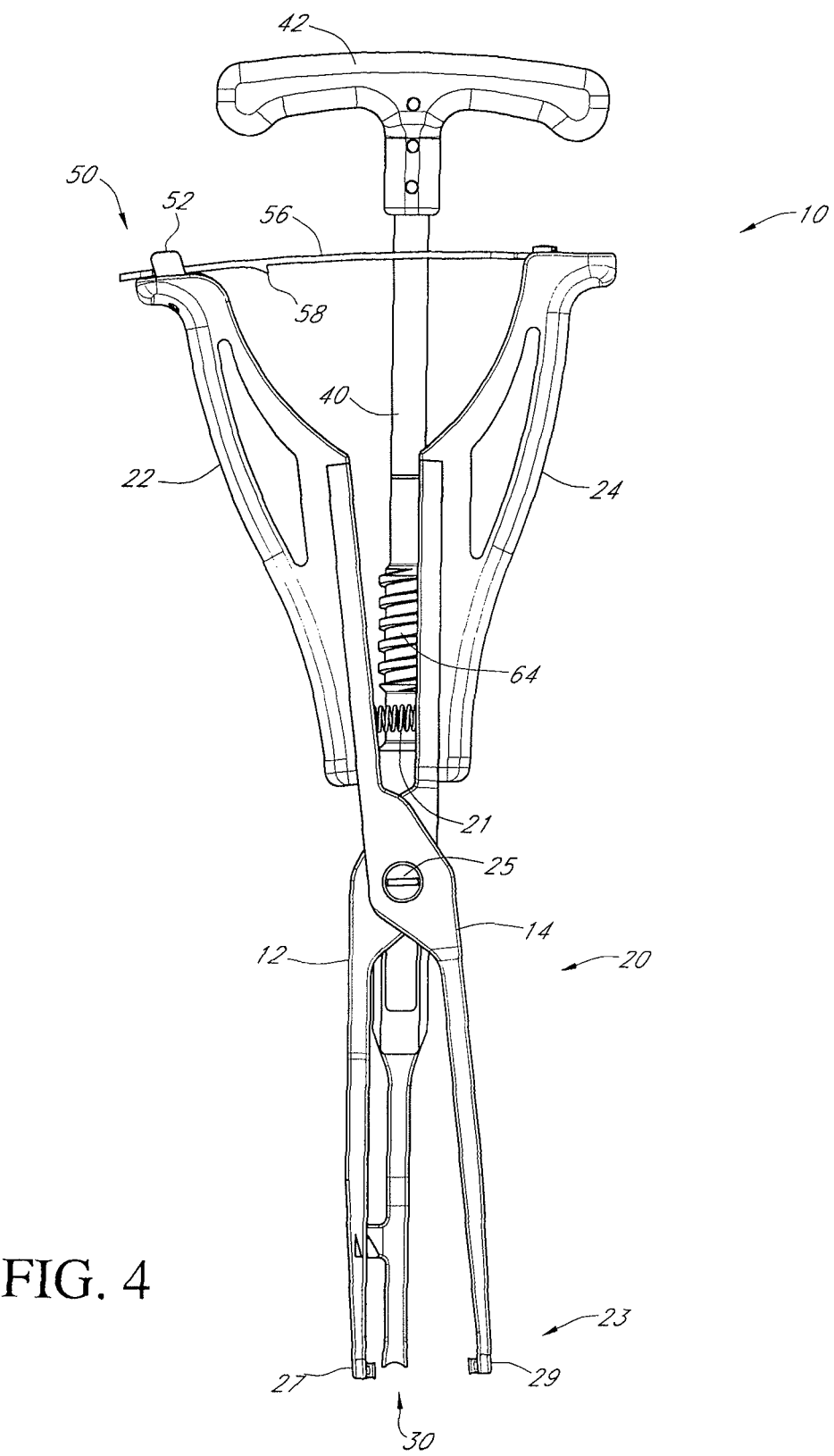
FIG. 4 shows a back view of a rod reducer instrument.

In some embodiments, the head 23 and grips 22, 24 can be connected by elongated members 12, 14, as shown in FIG. 4. The elongated members 12, 14 can be made of metal or other materials. The grips 22, 24 and/or head 23 can be made integrally with the elongated members 12, 14 or can be separate pieces that are attached to the elongated members 12, 14. As shown in FIG. 4, the head 23 can be made integrally with the elongated members 12, 14 and the grips 22, 24 can be separate pieces attached thereto.

Figure 6:
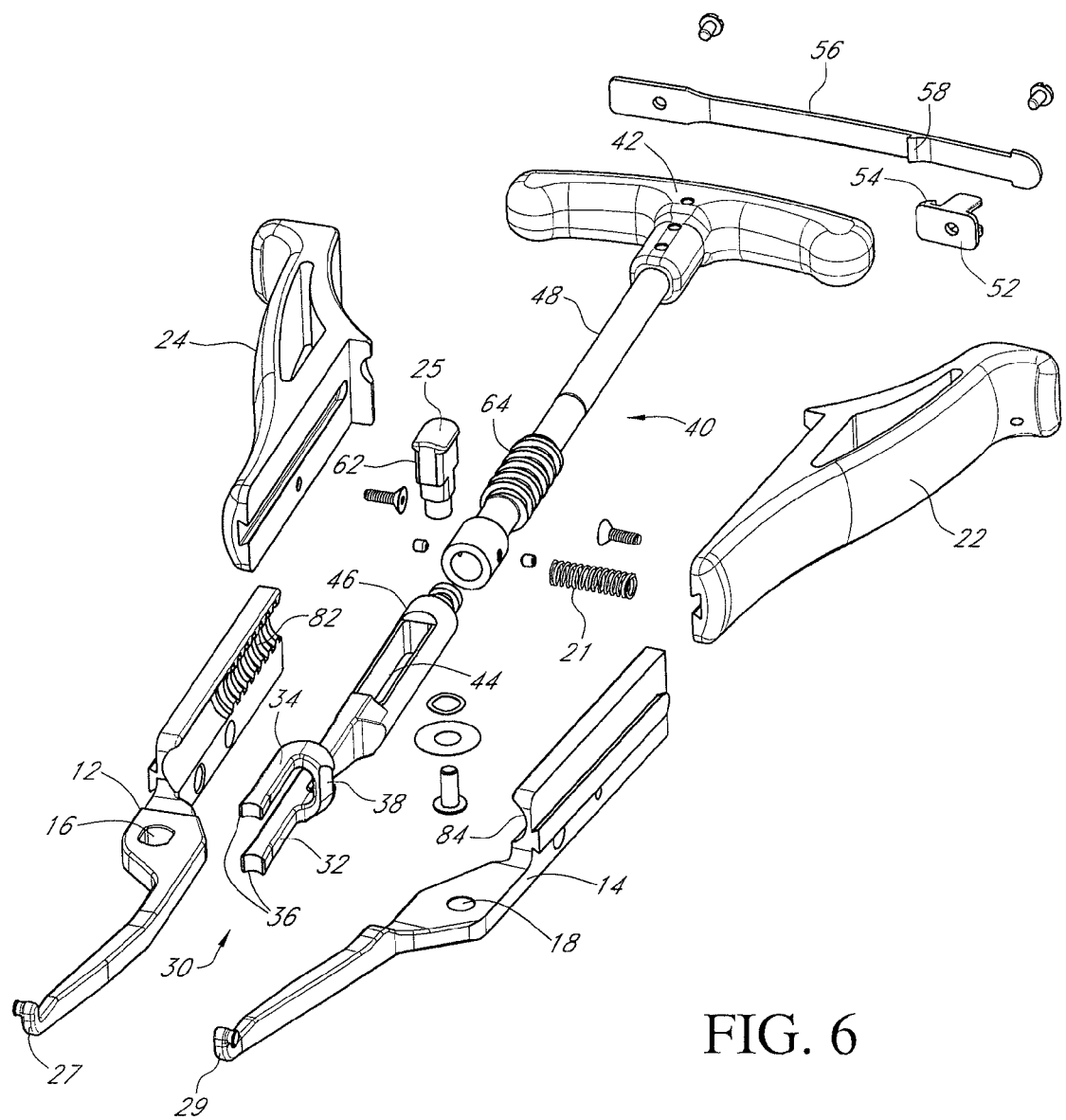
FIG. 6 is an exploded view of the rod reducer instrument of FIG. 5.

The elongated members 12, 14 can be connected by a pivot 25. The pivot 25 can allow the elongated members 12, 14 to rotate with respect to one another. The pivot 25 can be any device that allows elongated members 12, 14 to be connected and yet rotate along one axis. For example, the pivot 25 can be a rivet, a fastener, a snap-fit, etc. The pivot 25 can be a separate piece or pieces or can be made integrally with one of the elongated members 12, 14. In FIG. 6, the pivot 25 has a stepped diameter with a first circular diameter and then a second diameter with a first and second flat side and a first and second rounded side. This design allows the pivot 25 to fit securely into a non-circular hole 16 in one elongated member 12 and to fit into a circular hole 18 in the other elongated member 14. The pivot 25 can then be held in place with a washer and screw. In this configuration, the relationship between the pivot 25 and elongated member 12 can be maintained while elongated member 14 can rotate about the first circular diameter of the pivot 25. In other embodiments, the elongated member 14 can be maintained in relationship to the pivot 25 while elongated member 12 rotates.

In other embodiments, the pivot 25 can fit into two circular holes in the elongated members 12, 14 and all pieces can rotate with respect to one another. In still other embodiments, the elongated members 12, 14 can have non-circular holes 16, 18 which the pivot 25 can fit into, and the pivot 25 can be such so as to allow its parts to rotate in respect to itself. Thus, when the pivot 25 is inserted into the elongated members 12, 14 the pivot can rotate and change the relationship of the members 12, 14.

The pliers 20 is an instrument that can convert a power grip (e.g. the curling of the fingers into the palm of the hand) into a precision grip, directing the power of the hand's grip in a precise fashion onto the object(s) to be gripped. In the embodiments of the pliers 20 that comprise a spring 21, the precision grip can be further enhanced by providing a slight outward force on the pliers 20, i.e. a force resistive to the closing of the pliers 20, caused by the presence of the spring 21. The grips 22, 24 can be long relative to the jaws 27, 29 of the pliers 20. The two grips 22, 24 and elongated members 12, 14 can thus act as levers with a mechanical advantage, increasing the force applied by the hand's grip and concentrating it on a work piece, such as a fixation element 2.

A shaft 40 of the rod reducer instrument 10 will now be described. A shaft 40 can comprise a handle 42 and a pushing member 30. The handle 42 and pushing member 30 can be at opposite ends of the shaft 40. The handle 42 can be used by the user to cause a downward force on the pushing member 30. This downward force can force a rod 4 into engagement with a fixation element 2. The handle 42 can be a T-shaped handle, contoured to fit a user's hand, as shown in the figures. Other shapes and designs of a handle 42 can also be used.

Still looking to FIG. 6, a pushing member 30 can comprise a first leg 32 for engaging a rod 4. The pushing member 30 can further comprise a second leg 34 for engaging the rod 4. In other embodiments, the pushing member 30 can comprise a plurality of legs for engaging the rod 4. The leg(s) 32, 34 can have a first end 36 configured to engage the rod 4. The first end 36 can be shaped to correspond to the shape of the rod 4. As shown, the first end 36 can be concave. A concave first end 36 can be useful to more fully engage a round rod or a rod with a rod top surface. According to some embodiments, the first end 36 can only engage a top surface of the rod 4.

The first leg 32 can be inline with a central longitudinal axis of the shaft 40 as shown in FIG. 6. In other embodiments, one or more legs can be parallel to the central longitudinal axis of the shaft 40, such as second leg 34 in FIG. 6. In other embodiments, one or more legs can be partially inline with the shaft 40 or inline with one axis of the shaft 40 but not necessarily with other axes of the shaft 40. As illustrated in FIG. 6, the first leg 32 can form an end of the shaft 40 with the second leg 34 parallel to the first leg 32 and connected by a connecting member 38. The use of a leg or legs on the pushing member 30 can provide many benefits, for example, the legs can be close to the fixation element and yet still allow access to the fixation element. This can be important especially where the fixation element includes a top member configured to close on the rod and lock the rod and fixation element in an engaged position. In addition, the pushing member 30 can be sized to fit between the gripping jaws 27, 29 of the pliers 20. This can allow the force of the pushing member 30 to be directed more closely to the area of the rod 4 and fixation element 2 that are being engaged.

A rod reducer 10 can further comprise a slot 44 and a fixed pin 62. The fixed pin 62 can be used with the slot 44 to connect the shaft 40 to the pliers 20. The slot 44 and fixed pin 62 can also allow the shaft 40 to move in relation to the pliers 20. For example, when the pliers 20 are secured to a fixation element 2 the slot 44 can allow the shaft 40 to move in an upwards or downwards direction. According to some embodiments, a shaft 40 with a slot 44 can be used in this way to apply a downward force on the handle 42 to cause a rod 4 to engage with a fixation element 2. A rod reducer 10 according to other embodiments can connect a shaft 40 and a pliers 20 using other methods to achieve similar results as described above.

According to some embodiments a fixed pin 62 and a pivot 25 can be combined in one integral piece. As shown in FIG. 6, a combined fixed pin 62 and pivot 25 can have a stepped diameter creating essentially three different sized outer perimeters. One perimeter can correspond with the slot 44, one perimeter can correspond with elongated member 12 and one perimeter can correspond with elongated member 14. Other variations for the design of a combined fixed pin 62 and pivot 25 are also possible. In other embodiments, the pivot 25 and fixed pin 62 can be separate pieces.

The fixed pin 62 can be round, square or have other shapes. One benefit of having a shape with two opposing flat sides, such as a square or a rectangle is that an orientation of the shaft 40 can be maintained in relation to the pliers 20. This can be beneficial when, for example, the rod reducer 10 is configured to secure itself over a fixation element 2 in alignment with a channel in the fixation element 2 for engaging a rod 4 so that the rod reducer 10 can properly align and engage the rod 4 with the fixation element 2. According to other embodiments, a round fixed pin 62 can be used or in still other embodiment a fixed pin 62 can be configured to rotate in place. A round or rotating fixed pin 62 can be beneficially used to adjust an alignment between a rod reducer instrument 10 engaged with a fixation element 2 and a rod 4 so that the rod reducer 10 can properly force r the rod 4 into engagement with the fixation element 2. According to still other embodiments, other mechanisms could be used to allow the shaft 40 and the pliers 20 to change a lateral relationship or a rotational relationship so as to better engage a rod 4 with a fixation element 2 and to direct the force of the pushing member 30 in the correct direction.

Figure 7:
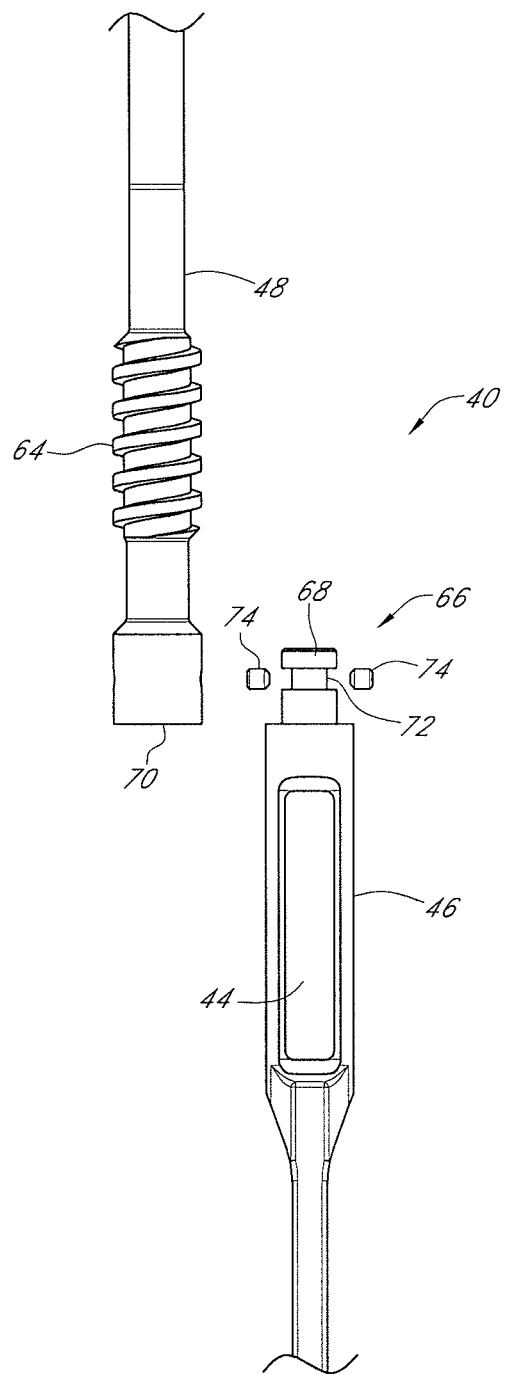
FIG. 7 is an exploded detail view showing a connecting mechanism that also can transfer a rotating motion on one part of a shaft into a linear motion on another part of the shaft.

According to some embodiments, a shaft 40 can be configured to transfer a rotational motion into a linear motion. As illustrated in FIGS. 3 and 7, a shaft 40 can comprise a first length 46 and a second length 48. The first length 46 and second length 48 can be configured to connect in such a way as to be able to convert a rotational motion of the shaft 40 into a linear motion of the shaft 40.

A shaft connection 66 can comprise a post 68 and a cap 70. The cap 70 can be configured to fit over the post 68. The shaft connection 66 can further comprise a groove 72 and a tongue 74. The tongue 74 can be configured to fit in the groove 72. The tongue 74 can also be configured to rotate within the groove 72, thereby allowing the second length 48 to rotate on the first length 46. As shown in FIG. 7, the groove 72 is on the post 68 and the tongue 74 comprises two set screws which are screwed into sides of the cap 70 to engage the groove 72 and also to secure the second length 48 to the first length 46. Other configurations are also possible, for example, the cap 70 could have an integral internal tongue 74, the cap 70 and post 68 could be forced together forming an interference type fit with sufficient clearances to allow the second length 48 to rotate on the first length 46. In other embodiments, the first length 46 and second length 48 are not direct connected but are aligned such that a downward force on the second length 48 whether caused by a rotational or a linear movement can cause a downward force on the first length 46.

As mentioned previously, the shaft 40 can experience a downward force to engage the pushing member 30 with a rod 4 and to force the rod 4 into engagement with a fixation element 2. The downward force experienced by the shaft 40 can be caused in many different ways. In a preferred embodiment a rotational movement of the handle 42 is converted into the downward force. A shaft 40 can comprise threads 64 so that the shaft 40 can act as a screw.

A screw is a shaft with a helical groove or thread formed on its surface and provision at one end (such as handle 42) to turn the screw. A screw can be used as a simple machine to translate torque into linear force. A screw can allow a tremendous amount of pressure to be applied with a fairly small amount of work. The ratio of threading determines the mechanical advantage of the machine. More threading, i.e. smaller pitch of the screw, increases the mechanical advantage. The pitch is the distance between two corresponding points on adjacent threads.

Figure 5:
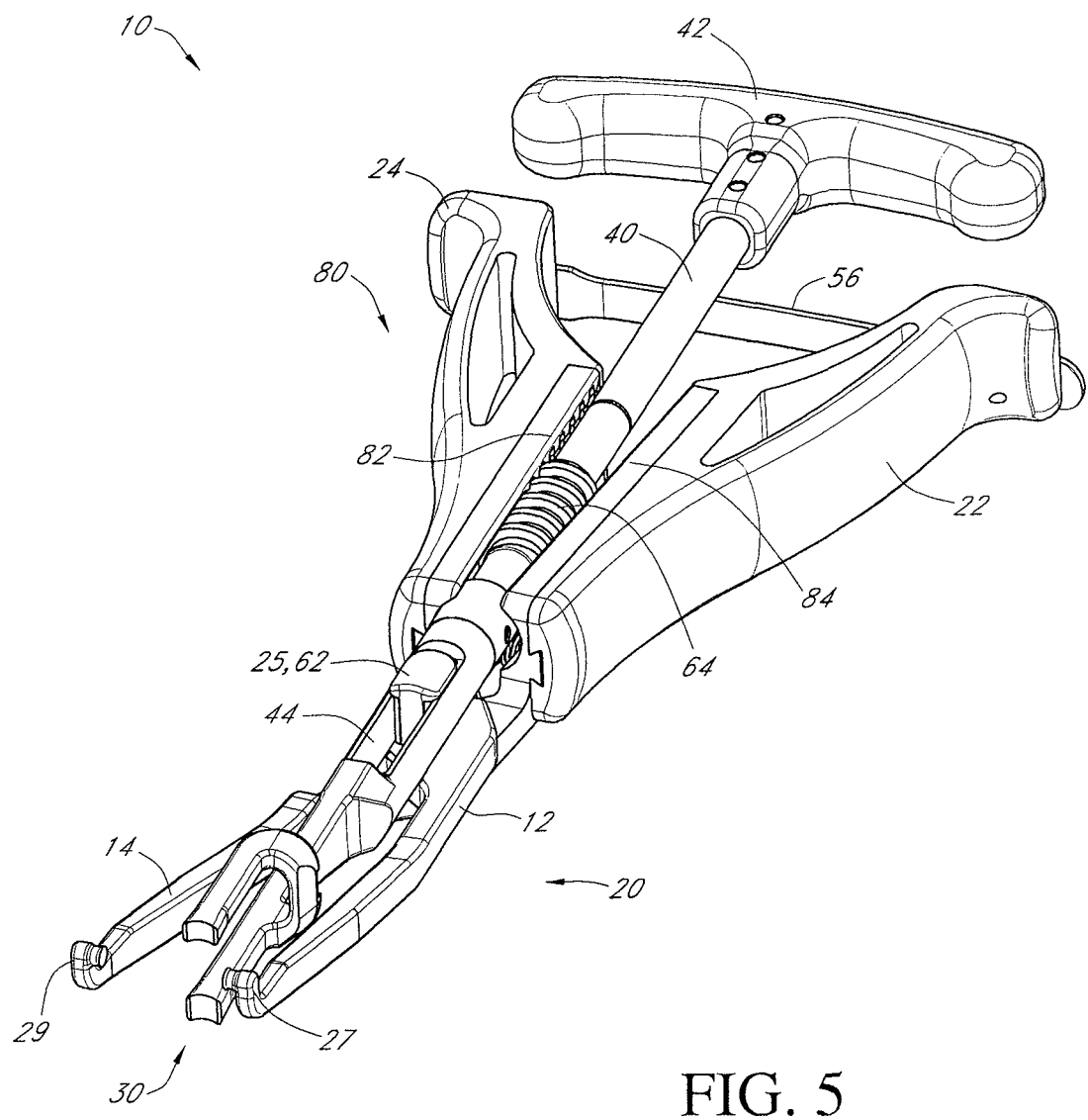
FIG. 5 is a bottom front perspective view of the rod reducer instrument.

Looking now at FIGS. 5 and 6, one embodiment of a rod reducer instrument 10 with a shaft 40 comprising threads 64 will be described. A rod reducer 10 can comprise threads 64 on a shaft 40 and a corresponding threaded chamber 80. The threads 64 on shaft 40 can fit within the threaded chamber 80 and rotate within the chamber 80. In a preferred embodiment, the elongated members 12, 14 can comprise sides 82, 84 of the threaded chamber 80. In other embodiments, the grips 22, 24 can comprise sides 82, 84 of the threaded chamber 80. In still other embodiments the threaded chamber 80 can be a separate piece that is attached to the pliers 20 or that is connected to the fixed pin 62 and/or pivot 25.

Having the sides 82, 84 of the chamber 80 as part of elongated members 12, 14 can provide many benefits. For example, besides minimizing the part count of the rod reducer 10, the shaft 40 and the threaded chamber 80 can be more easily aligned to therefore more directly and precisely cause the force directed on the shaft 40 to be transferred to forcing the rod 4 into engagement with the fixation member 2. Where there are many pieces connected to one another, such as: a separate chamber 80 that is connected to the grips 22, 24 that are connected to the elongated members 12, 14 some of the force on the shaft 40 can be directed to the connections between the chamber 80 and grips 22, 24 for example, instead of to directly forcing the rod 4 into engagement with the fixation member 2. This can be a result of design tolerances and the imperfect fit that can be a reality in some manufacturing techniques. This also can allow the shaft 40 to be directly over the fixation element with the pliers 20 and pusher member 30 in an integral configuration. Thus, the pusher member 30 and pliers 20 can not just be two separate tools that are bolted together but can be an integrated and unified tool.

In additional embodiments, a rod reducer 10 can comprise an unthreaded channel for guiding the shaft and therefore the pushing member. In some embodiments, the unthreaded channel can be below the threaded channel. In other embodiments, the rod reducer 10 can comprise a rack and pinion. The rack and pinion can convert a rotational movement into a linear movement to cause the shaft 40 to move in an downwards or upwards movement.

A rod reducer instrument 10 can also comprise a pliers lock 50. A pliers lock 50 can be a mechanism which can secure the pliers 20 in a locked position. Examples of possible embodiments for a pliers lock 50 can include a band, a latch, a ratchet, a cable tie, etc. A preferred embodiment is shown in FIG. 1. A pliers lock 50 can comprise a case 52 and a strap 56. The case can comprise a ratchet 54. The strap 56 can comprise a gear rack 58. The gear rack 58 can comprise one tooth or multiple teeth. The strap 56 can be inserted into the case 52 so that the gear rack 58 can engage the ratchet 54 to secure the pliers 20 in a locked position. The pliers lock 50 can comprise means to prevent the pliers lock 50 from becoming unlocked. The case 52 and strap 56 can be configured to allow the pliers lock 50 to have a locked position and an unlocked position wherein in some embodiments the unlocked position can be attained both before and after the pliers lock 50 has attained the locked position.

Figure 8:
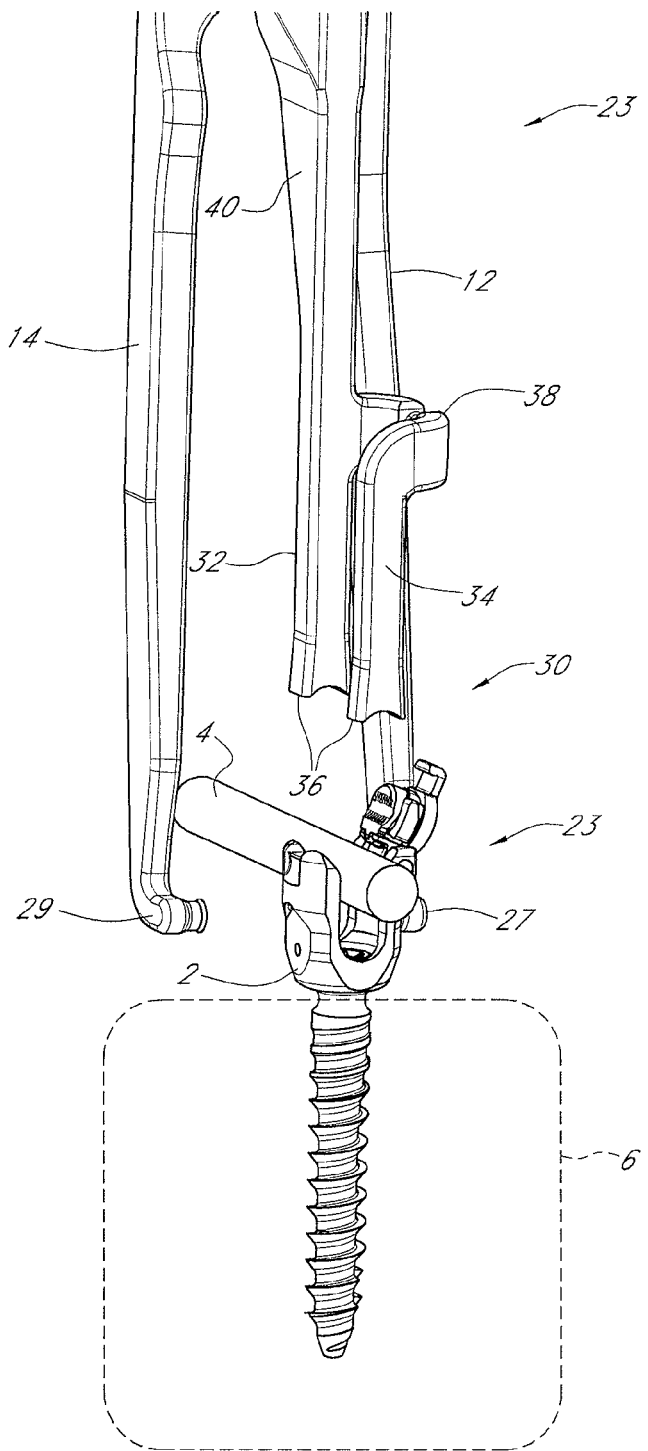
FIG. 8 shows a rod reducer instrument, a fixation element implanted in a bone and a rod.
Figure 9:
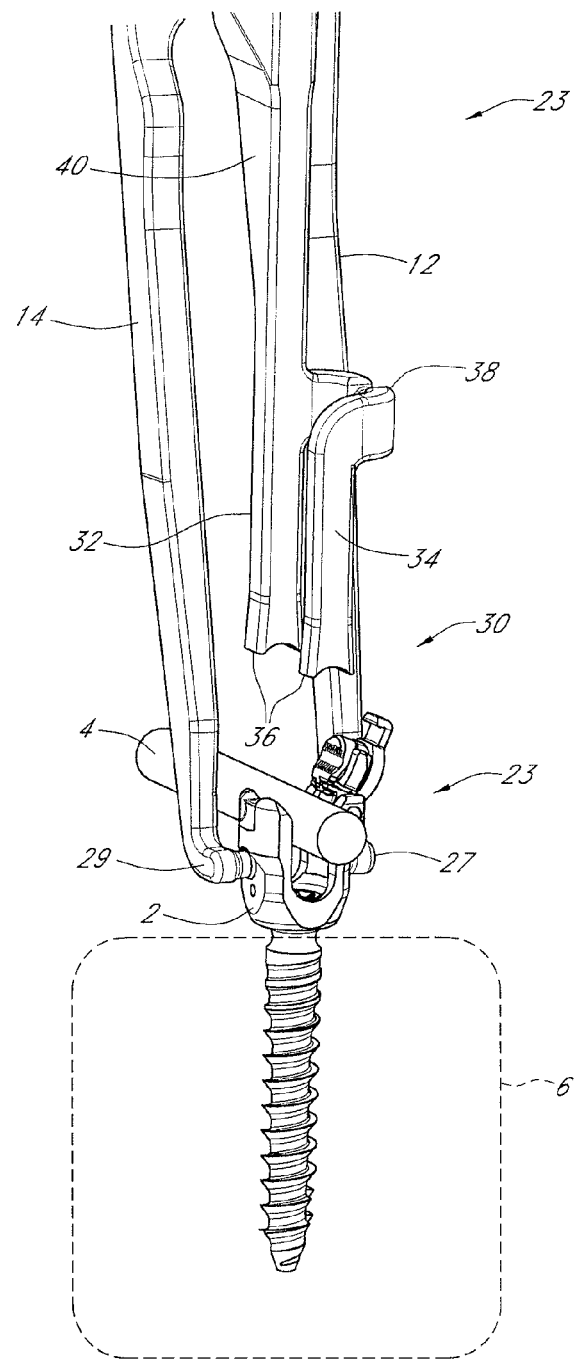
FIG. 9 shows a rod reducer instrument engaged with a fixation element.
Figure 10:
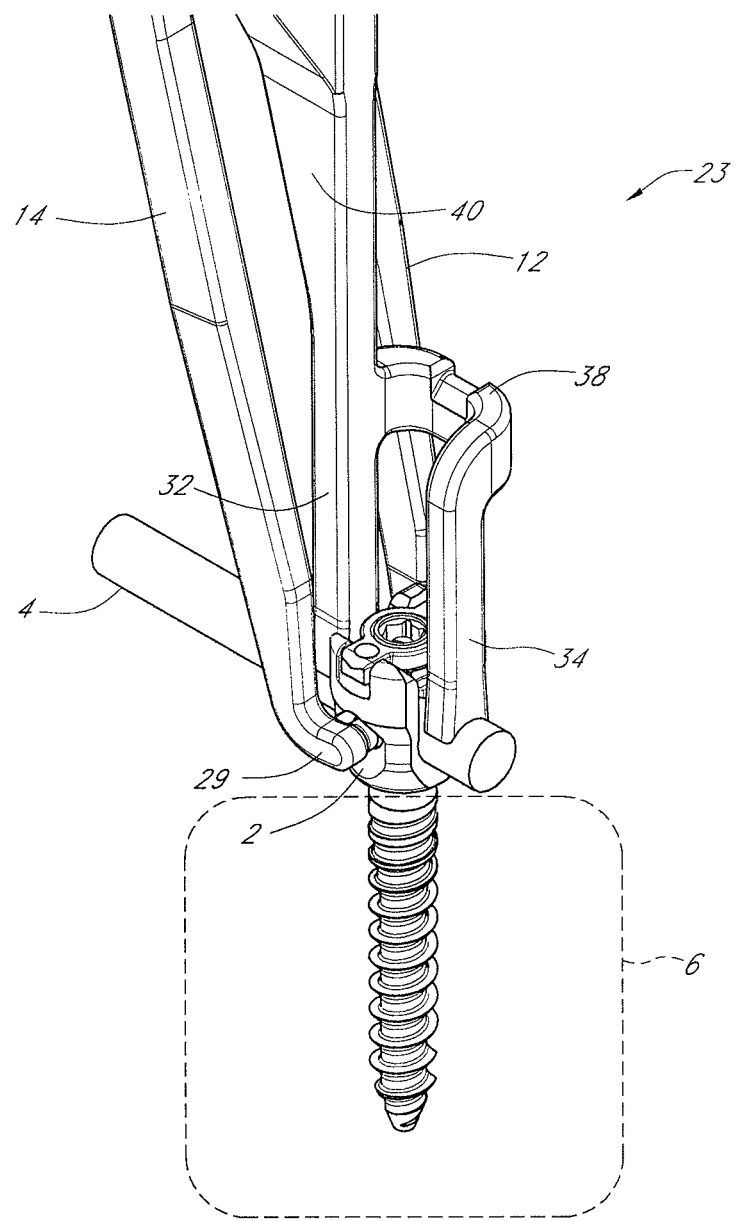
FIG. 10 illustrates a rod reducer instrument engaged with a fixation element where the rod reducer instrument has forced a rod into engagement with the fixation element.

Method of reducing a rod will now be described with reference to FIGS. 8-10. FIG. 8 shows a fixation element 2 that has been implanted in a bone 6. A rod 4 can be placed above a channel in fixation element 2. A rod reducer instrument 10 can be brought into contact with the fixation element 2. A position of a shaft 40 and pushing member 30 can be adjusted so as to not interfere with an interaction of the pliers 20 and the fixation element 2. As shown in FIG. 9, a pliers 20 of the rod reducer 10 can be secured onto the fixation element 2. A pliers lock 50 can be locked to secure the pliers 20 in engagement with the fixation element 2. In closing the pliers 20, a threaded chamber 80 can be created around threads 64 on the shaft 40 as chamber sides 84, 82 on elongated members 12, 14 are brought close together. A handle 42 can be rotated to cause a downward motion to be experienced by the shaft 40 and the pushing member 30. The pushing member 30 can engage a rod 4. The handle 42 can continue to be rotated to force the rod 4 into the channel in the fixation element 2 and thereby into engagement with the fixation element 2, as can be seen in FIG. 10. According to the type of fixation element 2 used, a top can be closed on the fixation element 2 to lock the rod 4 and fixation element 2 in the engaged position.

Other methods of reducing a rod can be performed utilizing other embodiments of a rod reducer instrument 10, or other embodiments of parts of the rod reducer instrument 10 or other embodiments of interactions between parts of the rod reducer instrument 10, as described herein.

The rod reducer instruments of the present invention are preferably made of a sturdy biocompatible material such as stainless steel using standard fabrication techniques for medical grade instruments. However, other biocompatible materials are also contemplated.

Although certain embodiments, features, and examples have been described herein, it will be understood by those skilled in the art that many aspects of the methods and devices shown and described in the present disclosure may be differently combined and/or modified to form still further embodiments. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present invention. Thus, it is intended that the scope of the present invention should not be limited by the particular embodiments described above, but should be determined only by a fair reading of the claims that follow.

What is claimed is:

1. A rod reducer instrument for use in orthopedic surgery comprising:
    a pliers for gripping an orthopedic screw comprising:
        a pair of grips for opening and closing the pliers, the grips configured to combine to form a threaded channel;
        a pivot about which at least one of the grips rotates, a fixed pin extending from the pivot; and
        a head having gripping jaws;
    a pushing member for forcing a rod into engagement with the orthopedic screw;
    a threaded shaft; and
    a shaft handle, wherein the threaded channel engages the threaded shaft when the pliers are closed and the shaft handle rotates the threaded shaft and thereby cause the pushing member to experience a linear motion;
    wherein the pushing member comprises an orifice that engages the fixed pin, the fixed pin extending at least partially into the orifice and guides the linear movement of the pushing member.

2. The rod reducer of claim 1 wherein one side of one of the pair of grips forms part of the threaded channel and one side of the other of the pair of grips forms the other part of the threaded channel.

3. The rod reducer of claim 1, wherein the pushing member is between the gripping jaws.

4. The rod reducer of claim 1, wherein the pushing member is configured to engage only a top of the rod.

5. The rod reducer of claim 1, further comprising a pliers lock configured to lock the pliers in gripping engagement with the orthopedic screw.

6. The rod reducer of claim 5, wherein the pliers lock comprises a ratchet and a strap with a gear rack.

7. The rod reducer of claim 1, wherein the pair of grips further comprise an unthreaded channel for guiding the pushing member.

8. The rod reducer of claim 1, further comprising a rotational joint connecting the pushing member and the threaded shaft.

9. The rod reducer of claim 1, wherein the pushing member comprises first and second legs configured to engage the rod.

10. The rod reducer of claim 1, further comprising a spring.

11. A rod reducer instrument for use in orthopedic surgery comprising:
    a pliers for gripping an orthopedic screw comprising:
        first and second elongated members;
        a pair of grips for opening and closing the pliers;
        a pivot about which at least one of the first and second elongated members rotates, a pin extending from the pivot; and
        a head having gripping jaws;
    a pushing member between the gripping jaws that forces a rod into engagement with the orthopedic screw, the pushing member comprising a slide that engages the pin on the pivot of the pliers wherein the pin extends into the slide and guides the linear movement of the pushing member; and
    a handle configured to turn in a circular rotation;
    wherein the rod reducer is configured to convert the circular rotations of the handle into a linear motion experienced by the pushing member and to thereby force the rod into engagement with the orthopedic screw.

12. The rod reducer of claim 11, further comprising a threaded shaft, wherein the first and second elongated members are configured to form a threaded channel to engage the threaded shaft when the grips are closed.

13. The rod reducer of claim 11, wherein the pushing member comprises first and second legs configured to engage the rod.

14. The rod reducer of claim 11, wherein the pivot has a stepped outer perimeter with a first step outer perimeter having a circular diameter so that the first elongated member can rotate about the pivot, a second step outer perimeter configured to substantially conform within an orifice in the second elongated member, the second elongated member not rotating about the pivot and a third step outer perimeter configured to engage the pushing member, the pushing member being slidable upon the pivot.

15. The rod reducer of claim 14, wherein the pushing member is configured to not rotate about the pivot.

16. A method of reducing a rod in orthopedic surgery comprising:
    engaging a rod with a pushing member of a rod reducer instrument, the rod reducer further comprising a pliers comprising a pin extending from the pivot of the pliers, and a handle;
    closing the pliers to grip an orthopedic screw and to form a threaded channel with the pliers;
    rotating the handle in a continuous circular rotation to cause a downward linear movement of the pushing member through the threaded channel, wherein an orifice in the pushing member engages the pin, the pin extending into the orifice to guide the linear movement of the pushing member; and
    forcing the rod into engagement with the screw.

17. The method of claim 16, further comprising locking the pliers in gripping engagement with the orthopedic screw.

18. The method of claim 17, further comprising unlocking the pliers from gripping engagement with the orthopedic screw and thereby releasing engagement with the rod.

19. The method of claim 16, further comprising adjusting a relationship between the pushing member and the pliers.

20. The method of claim 16, wherein the step of rotating the handle further comprises causing a downward linear movement of the pushing member between the jaws of the pliers.

* * * * *